(12) United States Patent
Hall et al.

(10) Patent No.: US 11,635,424 B2
(45) Date of Patent: Apr. 25, 2023

(54) MEDICAL TOILET WITH APTAMER SENSORS TO ANALYZE URINE (71) Applicant: Medic, Inc., Provo, UT (US)

(72) Inventors: David R. Hall, Provo, UT (US); Dan Allen, Springville, UT (US); Conrad Rosenbrock, Provo, UT (US); Daniel Hendricks, Provo, UT (US); Andrew Nguyen, Provo, UT (US); Steven J. M. Butala, Provo, UT (US); Travis Niederhauser, Mapleton, UT (US); Terrece Pearman, Draper, UT (US); Joe Fox, Spanish Fork, UT (US)

(73) Assignee: Medic, Inc., Provo, UT (US)

( * ) Notice: Subject to any disclaimer, the term of this patent is extended or adjusted under 35 U.S.C. 154(b) by 236 days.

(21) Appl. No.: 16/904,315

(22) Filed: Jun. 17, 2020

(65) Prior Publication Data
US 2020/0319159 A1 Oct. 8, 2020

Related U.S. Application Data (62) Division of application No. 15/589,403, filed on May 8, 2017, now abandoned.

(51) Int. Cl.
G01N 33/493 (2006.01)
G01N 33/487 (2006.01)
G01N 33/543 (2006.01)
G01N 21/64 (2006.01)
G01N 21/78 (2006.01)
A61B 5/00 (2006.01)
A61B 5/20 (2006.01)
A61B 10/00 (2006.01)
(Continued)

(52) U.S. Cl.
CPC ......... *G01N 33/493* (2013.01); *A61B 5/0071* (2013.01); *A61B 5/1455* (2013.01); *A61B 5/1468* (2013.01); *A61B 5/14507* (2013.01); *A61B 5/207* (2013.01); *A61B 5/6887* (2013.01); *A61B 10/007* (2013.01); *G01N 21/645* (2013.01); *G01N 21/6428* (2013.01); *G01N 21/78* (2013.01); *G01N 33/48792* (2013.01); *G01N 33/5438* (2013.01); *G01N 27/3276* (2013.01); *G01N 2021/6419* (2013.01); *G01N 2021/6432* (2013.01)

(58) Field of Classification Search
None
See application file for complete search history.

(56) References Cited

FOREIGN PATENT DOCUMENTS

JP H08-262017 A * 10/1996

* cited by examiner

Primary Examiner — J. Christopher Ball (57) ABSTRACT

We disclose an in-toilet urinalysis system which includes a system for collection urine and for analysis of urine components using aptamer technology. Urine collection system may dispense urine into cuvettes, channels, or other containers that include aptamers. The aptamers may detect target molecules in urine. The aptamers may measure urine analytes, detect excreted drugs or drug metabolites, or disease markers. Upon binding to the target molecule, the aptamers may produce a signal which a sensor in the toilet may detect. In some embodiments, the signal may be electrochemical, fluorescent, or colorimetric. The measurements obtained from analysis of the urine may be used to assess a user's health or diagnose disease. In some embodiments, the measurements are stored in a controller which may transmit the measurements to a healthcare provider for assessment.

19 Claims, 7 Drawing Sheets (51) Int. Cl.
*A61B 5/145* (2006.01)
*A61B 5/1455* (2006.01)
*A61B 5/1468* (2006.01)
*G01N 27/327* (2006.01)

MEDICAL TOILET WITH APTAMER SENSORS TO ANALYZE URINE

CROSS-REFERENCE TO RELATED APPLICATIONS

This application is a divisional application of U.S. patent application Ser. No. 15/589,403 titled "Medical Toilet with Aptamer Sensors to Analyze Urine" filed on May 8, 2017.

BACKGROUND

Field of the Invention

This disclosure relates to devices and methods for analyzing urine samples to assess health status and to aptamer technology.

Background of the Invention

Laboratory tests, including analysis of urine analytes, can be inconvenient and require a user to visit a healthcare facility. In the case or urinalysis, the collection process in a specimen cup or test strip on which a user may urinate directly may be unsanitary resulting in spilled or dripped urine. A convenient and simple device for collecting and analyzing urine is needed. A device which may be used in a user's home without the need to visit a healthcare facility is even more desirable.

Aptamer technology has provided a wealth of mechanisms which may be used to detect drugs, proteins, and other analytes in biological fluids. It is desirable to adapt aptamer technology to make it available for in-home analysis of bodily fluids. Doing so would make aptamer technology available to more users in a convenient and discreet platform.

BRIEF SUMMARY OF THE INVENTION

We disclose an in-toilet urinalysis system which uses aptamer-mediated sensors to detect analytes in a user's urine. To use the disclosed system, a user may urinate normally into a toilet bowl. The urine may contact one or more aptamers within the medical toilet. The aptamers may include at least one binding site for one or more components of a user's urine. The aptamers may produce an electrochemical signal, a fluorescent signal, or a colorimetric signal. The medical toilet may include a detection device which may detect the signal produced by the bound aptamers.

In some embodiments, the medical toilet includes a urine capture reservoir and fluid handling system which may collect urine and direct it to a measurement cell.

In some embodiments, the medical toilet includes multiple aptamers which, together, may detect a plurality of components in a user's urine. Consequently, the medical toilet may screen a urine sample for a panel of urine analytes, proteins, drugs, or drug markers.

In some embodiments, the medical toilet includes a controller which may store data and which may include computer readable medium. The controller may collect data comprising signals produced by the aptamers and it may then analyze the signals. This may be particularly useful when assaying a urine sample using a panel of aptamers which detect different urine components.

DETAILED DESCRIPTION OF THE INVENTION

Definitions

Toilet, as used herein, means a device that collects biological products of a mammal, including urine and feces.

Medical toilet, as used herein, means a toilet that includes one or more medical devices and/or other analytical equipment which may be used to assess a user's health or diagnose disease.

User, as used herein, means any mammal, human or animal, from which a urine sample is deposited into the in-toilet urinalysis system disclosed herein and analyzed.

Nucleic acid, as used herein, means deoxyribonucleic acid, ribonucleic acid, or analogs thereof. Nucleic acid, as used herein, may mean a single stranded or double stranded molecule.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a medical toilet which includes an in-toilet urinalysis system. The in-toilet urinalysis system may include at least one aptamer sensor. The aptamer sensor may include at least one aptamer comprised of a nucleotide or peptide. In some embodiments, the aptamer is on a stable protein scaffold. In some embodiments, the aptamer may be in solution. The aptamer may emit a detectable signal which may be an electrochemical signal, a fluorescent signal, or a colorimetric signal. The aptamer may include aptamers and aptamer sensors as reviewed by Song, S., Wang, L., Li, J., Zhao, J., and Fan, C. (2008) Aptamer-based biosensors. Trends Analyt. Chem. 27, 108-117 which is hereby incorporated by reference in its entirety.

In embodiments in which the at least one aptamer emits an electrochemical signal, the medical toilet may include an electrochemical cell. The electrochemical signal may be an electric current. In some embodiments, the signal may be a change in a feature in a voltammetry curve. The change in a feature in a voltammetry curve may be a voltage shift or a change in a peak shape.

The electrochemical cell may include a bias or voltammetry circuit. The bias or voltammetry circuit may be connected to a reference electrode. The electrochemical cell may include a counter electrode and a functionalized electrode. The functionalized electrode may comprise a noble metal. The functionalized electrode may comprise a surface comprising a noble metal selected from the group consisting of gold, ruthenium, rhodium, palladium, silver, osmium, iridium, platinum, and combinations, mixtures, and alloys thereof.

The functionalized electrode may be bound to at least one aptamer.

The at least one aptamer may include one or more binding sites for one or more components of a user's urine. In some embodiments, the medical toilet may include multiple aptamers, each with different binding sites which bind to a different component of a user's urine. Consequently, the medical toilet may detect a plurality of urine components nearly simultaneously. For example, a user's urine may be analyzed using specific urine analyte panel. Alternatively, the user's urine may be tested for an array of pharmaceuticals or drug tags. In some embodiments, the aptamer may catalyze a chemical reaction when the component of the user's urine binds to the binding site. The chemical reaction may modify the component of the user's urine.

In embodiments in which the at least one aptamer emits a fluorescent signal, the medical toilet may include a fluorescence spectrometer and at least one fluorescence cell. The medical toilet may include at least one aptamer, and each aptamer may include a binding site which binds a component of a user's urine.

The fluorescence spectrometer may include an excitation light source, a urine sample flow path, and a fluorescence detector. The excitation light source may direct light toward the urine sample flow path. The fluorescence detector may receive non-specular light from the urine sample flow path.

In some embodiments, the aptamer includes both a fluorophore and a quencher. The fluorophore and quencher may be bound to the nucleotide or peptide of the aptamer. When the component of the user's urine binds the binding site in the aptamer, the nucleotide or peptide may undergo a conformational change. This conformational change may move the quencher further away from the fluorophore. The fluorophore may then emit a signal that the fluorescence detector may measure.

In some embodiments, the fluorescent aptamer may be in solution. The solution may be added to one or more fluorescence cells and mixed therein with a sample of a user's urine. The medical toilet may include a dispensing system which may deliver the aptamer solution into the one or more fluorescent cells. A controller may be connected to the dispensing system which may modulate which aptamer solution is dispensed into the one or more fluorescent cells.

Similar to the electrochemical aptamers described above, each of the fluorescent aptamers may include one or more binding sites for one or more components of a user's urine. The medical toilet may include multiple fluorescent aptamers, each with different binding sites which bind to a different component of a user's urine. Consequently, the medical toilet may detect a plurality of urine components nearly simultaneously. For example, a user's urine may be analyzed using specific urine analyte panel. Alternatively, the user's urine may be tested for an array of pharmaceuticals or drug tags.

In embodiments in which the at least one aptamer produces a colorimetric signal, the medical toilet may include an absorption spectrometer and at least one absorption cell. As with the electrochemical and fluorescent aptamers, the colorimetric aptamers may include one or more binding sites for one or more components of a user's urine. In some embodiments, the medical toilet may include multiple colorimetric aptamers, each with different binding sites which bind to a different component of a user's urine. Consequently, the medical toilet may detect a plurality of urine components nearly simultaneously. For example, a user's urine may be analyzed using specific urine analyte panel. Alternatively, the user's urine may be tested for an array of pharmaceuticals or drug tags.

The colorimetric aptamers may include a plurality of nanoparticles. The plurality of nanoparticles may be a first color when bound to the at least one aptamer. In contrast, the plurality of nanoparticles may be a second color when aggregated to each other. The absorption spectrometer may measure the change in color which functions as a signal that the aptamers have bound to their target urine component. Embodiments of colorimetric aptamers include those reviewed by Song et al. (2008). In an example, the nanoparticles are gold nanoparticles. Other colorimetric aptamers may include nanoparticles of noble metals such as ruthenium, rhodium, palladium, silver, osmium, iridium, platinum, and combinations, mixtures, and alloys thereof.

Similar to the fluorescent aptamers, the colorimetric aptamers may be in solution. The solution may be added to an absorption cell and mixed with a sample of a user's urine therein. The medical toilet may include a dispensing system which may deliver the aptamer solution into one or more absorption cells. A controller may be connected to the dispensing system which may modulate which aptamer solution is dispensed into the one or more absorption cells.

In any of the embodiments described above, the medical toilet may include a urine capture reservoir and a fluid handling system. The fluid handling system may include a channel which fluidly connects the urine capture reservoir to at least one electrochemical, fluorescent, or absorption cell. Some embodiments include a urine capture reservoir and capillary as disclosed in U.S. patent application Ser. No. 15/414,197 filed on Jan. 24, 2017 which is hereby incorporated by reference in its entirety. Other methods of capturing and handling urine are within the scope of this disclosure.

The medical toilet disclosed herein may include a controller. The controller may be connected to the functionalized electrode, the fluorescence spectrometer, the absorption spectrometer, or any device which measures a signal produced upon binding of a user's urine component to an aptamer. The controller may include computer readable medium which analyzes the signals. In embodiments in which the medical toilet includes multiple aptamers which detect a panel of components of a user's urine, the controller may store information about the library of aptamers and the computer readable medium may analyze the signals collected from the panel of aptamers.

Figure 1:
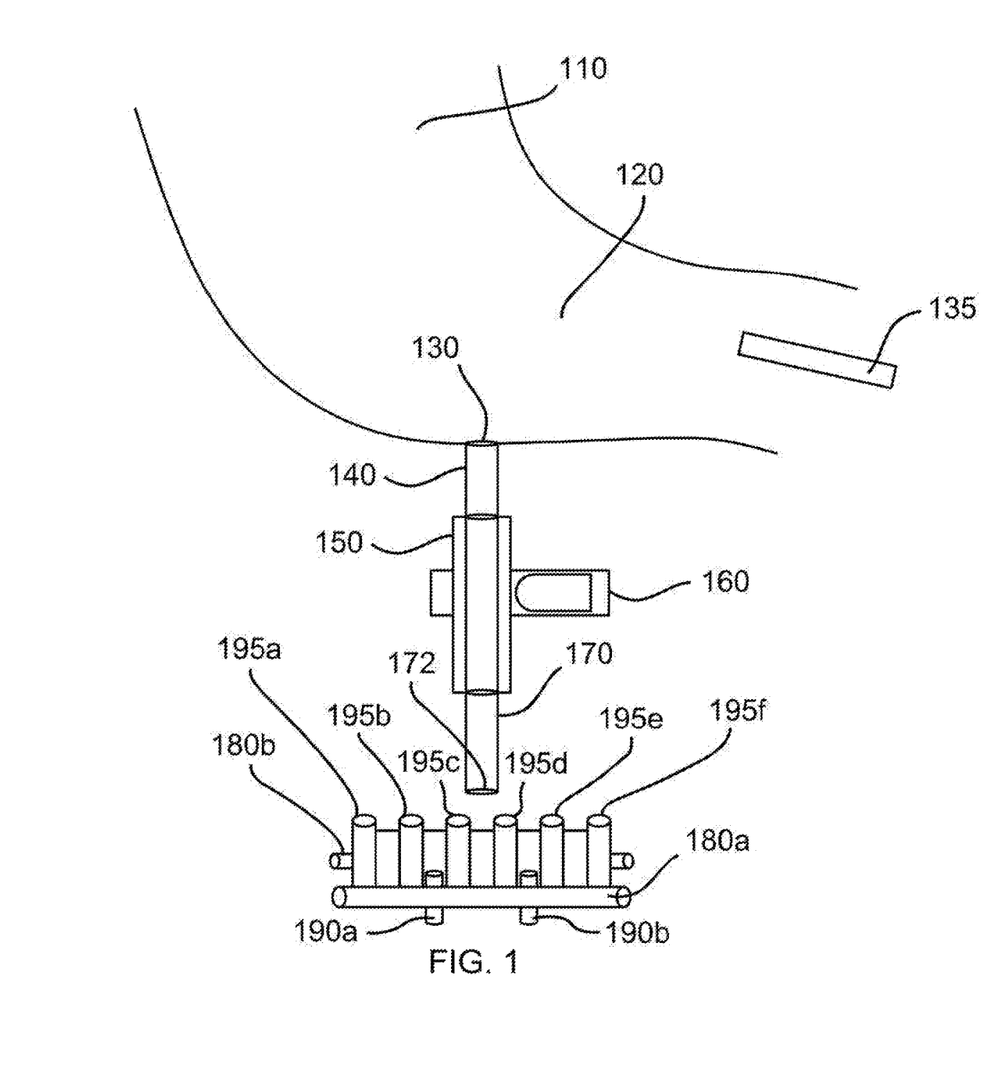
FIG. 1 is a cross-sectional view of an embodiment of the disclosed in-toilet urinalysis system delivering urine into a series of cuvettes.

Referring now to the drawings, FIG. 1 illustrates an embodiment of a urine capture reservoir and capillary system which may be used to collect a urine sample for analysis by the aptamer sensor. FIG. 1 shows a cross sectional view of an embodiment of a toilet bowl within a medical toilet. FIG. 1 also includes a series of cuvettes which may be part of an aptamer sensor according to the disclosure. A first end 110 and a second end 120 of a urine capture reservoir are shown. In the embodiment of FIG. 1, first end 110 is wider than second end 120. The relative widths of first end 110 and second end 120, as illustrated, may not be proportional. A channel is shown which includes two sections. First section 140 is open at both ends and defines orifice 130. Orifice 130 leads into the urine capture reservoir within the toilet bowl and collects urine. Second section 150 of the channel is connected to first section 140. First section 140 may include a noncompliant material which may be stainless steel, polyvinyl chloride (PVC) pipe, or other noncompliant polymer. Second section 150 may include a compliant material which may be compliant rubber.

The embodiment shown in FIG. 1 includes pinch valve 160 which is shown in its open state. When actuated, pinch valve 160 may compress section 150 thereby closing off the path of fluid through the orifice and into the channel. An open end of second section 150 is connected to capillary 170. Capillary 170 includes distal opening 172. A user's urine stream may be temporarily collected in the urine capture reservoir and enter orifice 130. The urine may travel through first end 140 and second end 150 of the channel and into capillary 170.

A series of cuvettes is shown below distal opening 172. The series of cuvettes include cuvettes 195a-f. Cuvettes 195a-f may be moved laterally along a track comprising track rails 180a and 180b. Track rail 180a includes 190a and 190b while track rail 180b includes grip rollers that are not visible from the view shown in FIG. 1. As the track moves cuvettes 195a-f laterally, each cuvette may be loaded with a urine sample which may be dispensed through distal opening 172. FIG. 1 also includes slit-shaped opening 135 which may collect urine for other analysis techniques.

Figure 2:
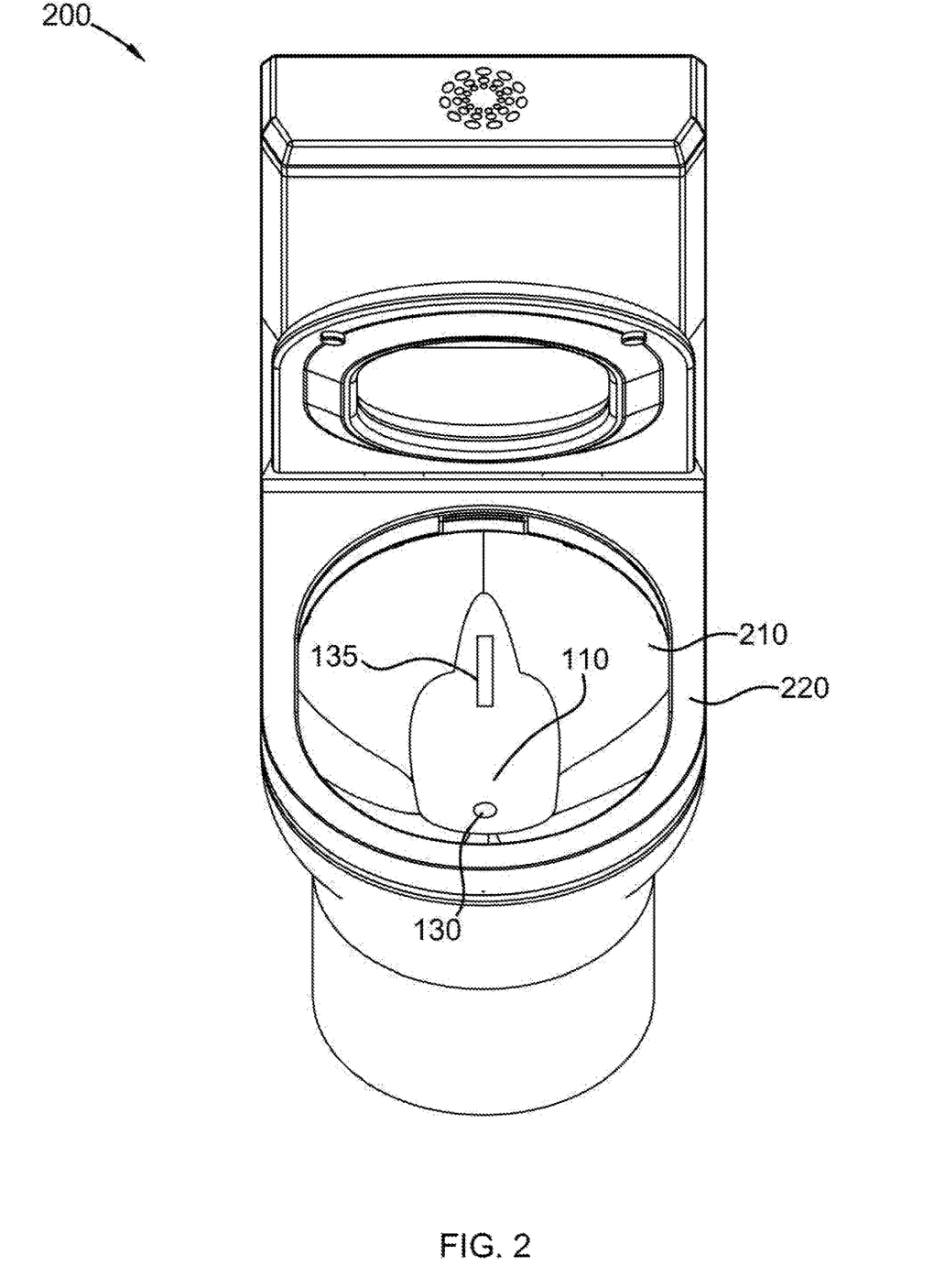
FIG. 2 is an aerial view of an embodiment of a toilet which includes the disclosed in-toilet urinalysis system.

FIG. 2 shows an aerial view of medical toilet 200 which is an embodiment of a medical toilet that includes the urine capture reservoir illustrated in FIG. 1. Medical toilet 200 includes toilet bowl 210 and toilet seat 220. A urine capture reservoir is shown within toilet bowl 210 which includes first end 110. Orifice 130 is shown at first end 110 and slit-shaped opening 135 is shown at the second end of the urine capture reservoir which is narrower than first end 110.

Figure 3A:
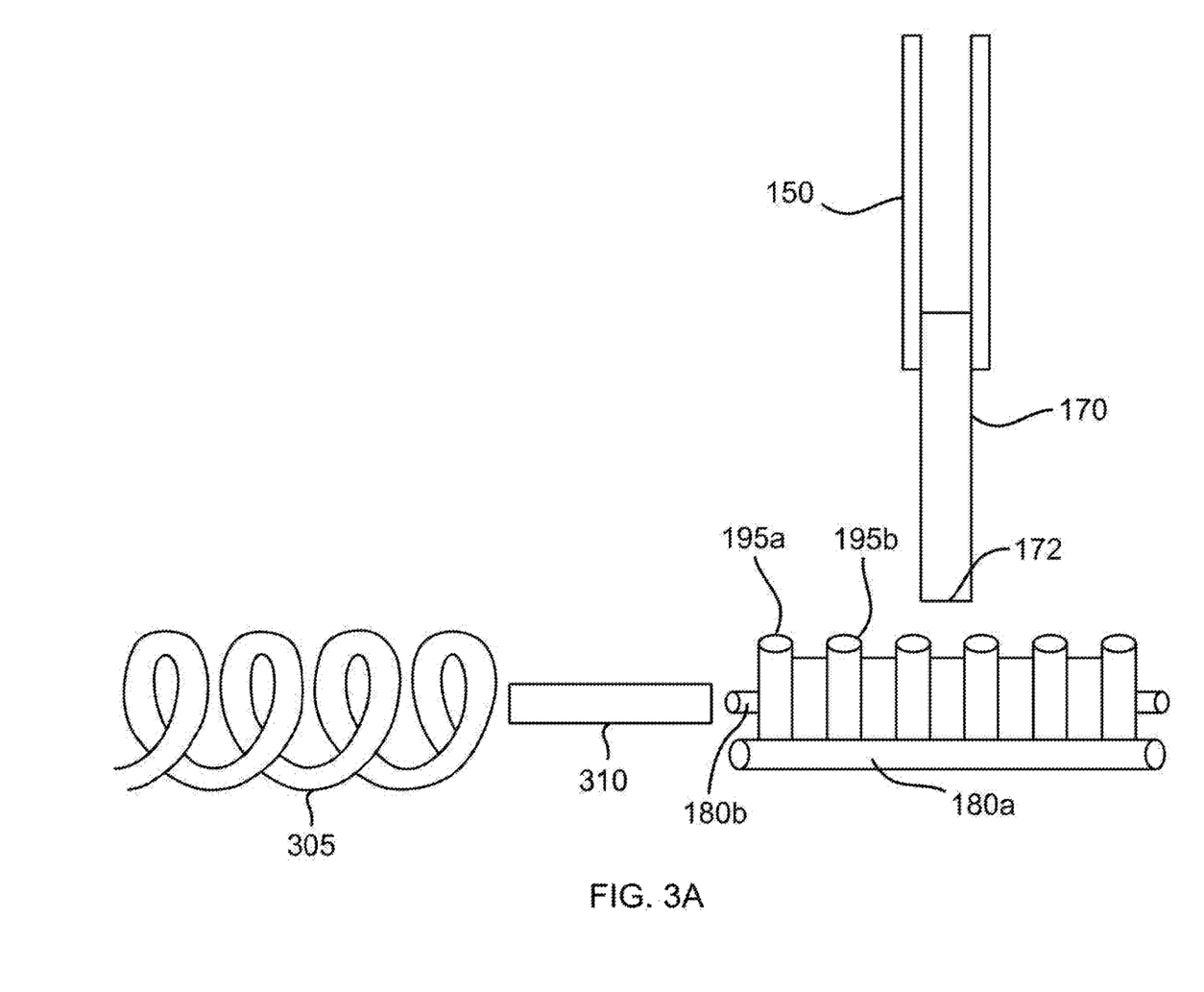
FIG. 3A is an embodiment of a portion of the in-toilet urinalysis system in which a solenoid moves the series of cuvettes past a capillary opening dispensing urine.

FIG. 3A includes an embodiment of a device for loading urine into a series of cuvettes which includes a solenoid. A series of cuvettes as shown in FIG. 1 are loaded between track rails 180a and 180b. The series of cuvettes is positioned below capillary 170. Solenoid 305 extends and applies force to push bar 310. Push bar 310 then applies force to cuvette 195a and pushes the series of cuvettes laterally past capillary 170. As solenoid 405 extends further, the series of cuvettes moves to the right on FIG. 3A so that each of cuvettes 195a-f are sequentially positioned directly below distal opening 172 and urine is dispensed into each of cuvettes 195a-f. Note that, for purposes of clarity, not all cuvettes are labeled in FIGS. 3A and 3B.

Figure 3B:
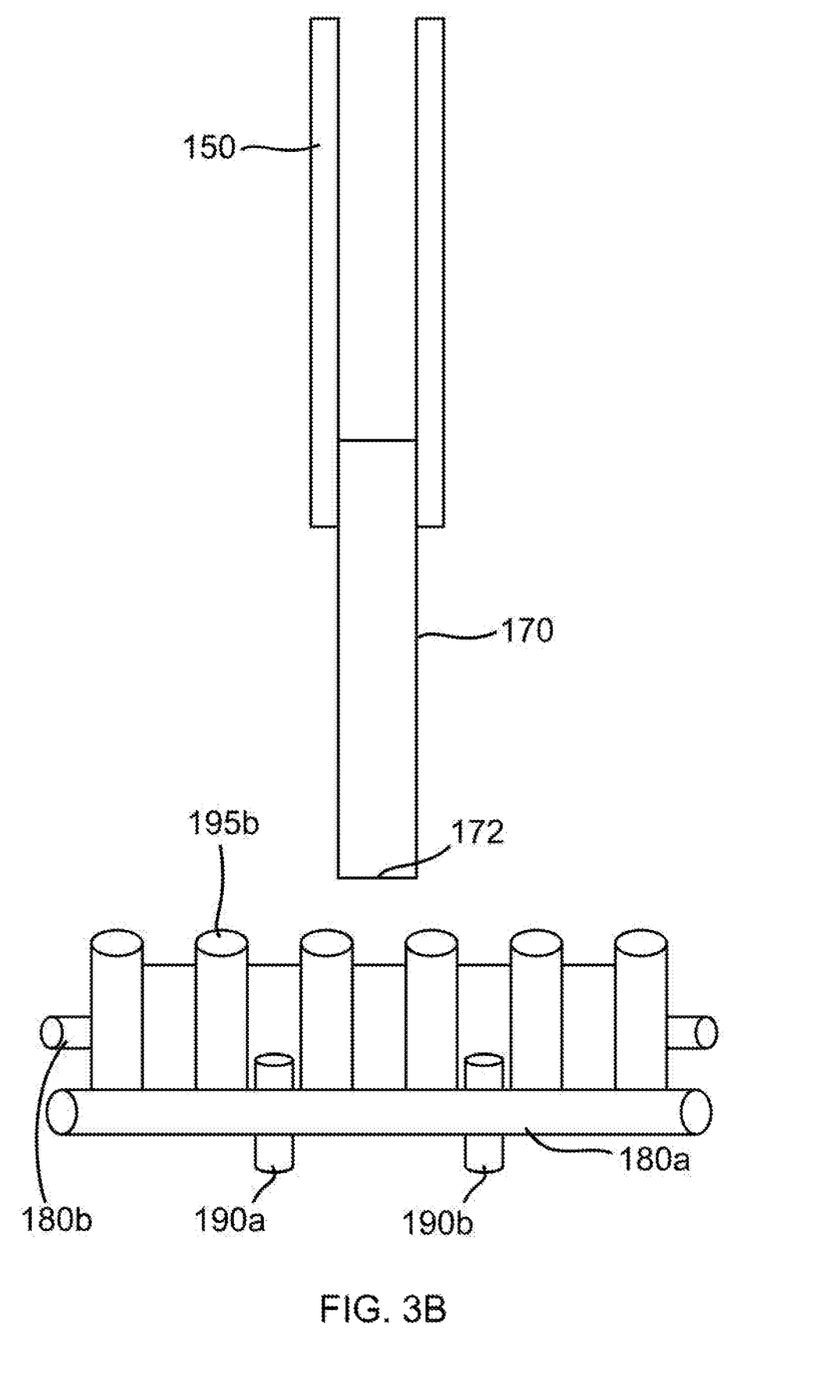
FIG. 3B is an embodiment of a portion of the in-toilet urinalysis system in which a track and grip rollers move the series of cuvettes past the capillary opening.

FIG. 3B illustrates another device which may be used to move the series of cuvettes shown in FIG. 1. This device includes track rails 180a and 180b. Grip rollers 190a and 190b are shown connected to track rail 180a. Another set of grip rollers may be positioned on the opposite side of the series of cuvettes and connected to track rail 180b. A motor causes the grip rollers to rotate and move the series of cuvettes laterally. As illustrated in FIG. 3B, cuvettes 195a-f (not all are labelled for purposes of clarity) are sequentially positioned below opening 172 of capillary 170 and receive a sample of urine for analysis by an aptamer sensor within each cuvette.

Figure 4A:
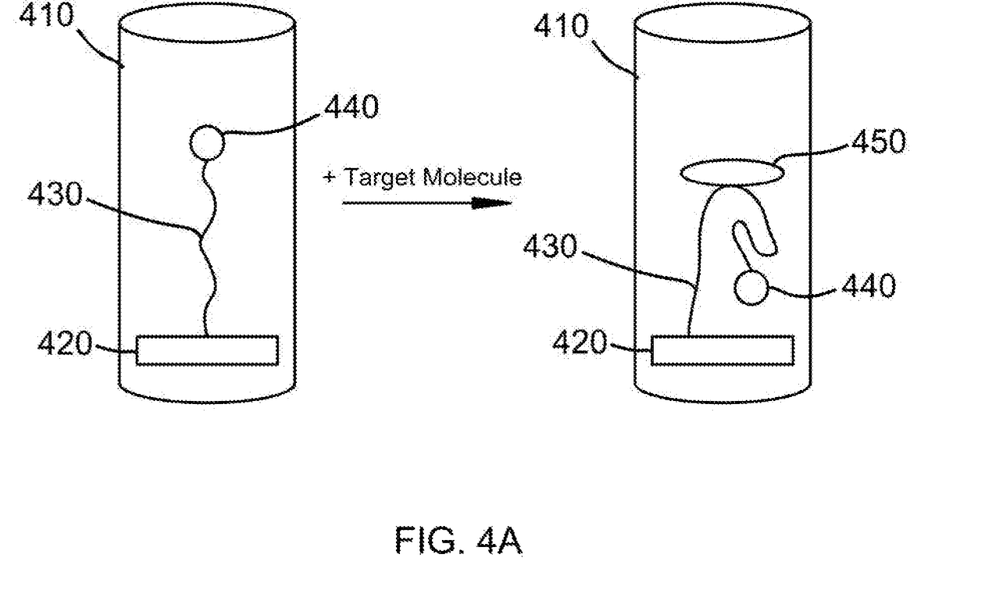
FIG. 4A illustrates an embodiment of an electrochemical aptamer sensor within a cuvette which may be included in the disclosed in-toilet urinalysis system.
Figure 4B:
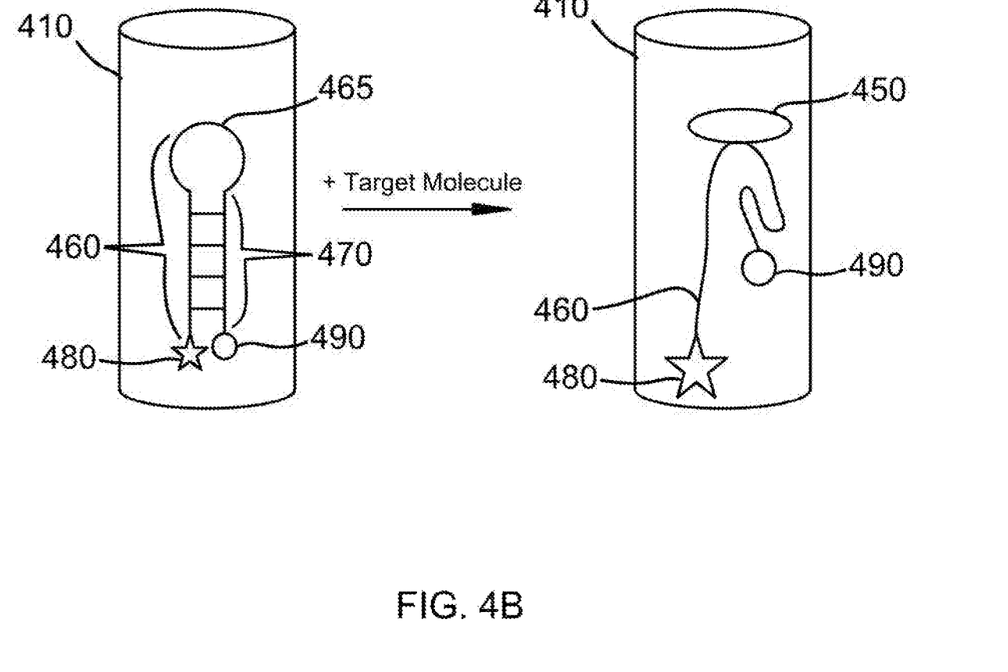
FIG. 4B illustrates an embodiment of an aptamer sensor within a cuvette which emits a fluorescent signal and which may be included in the disclosed in-toilet urinalysis system.
Figure 4C:
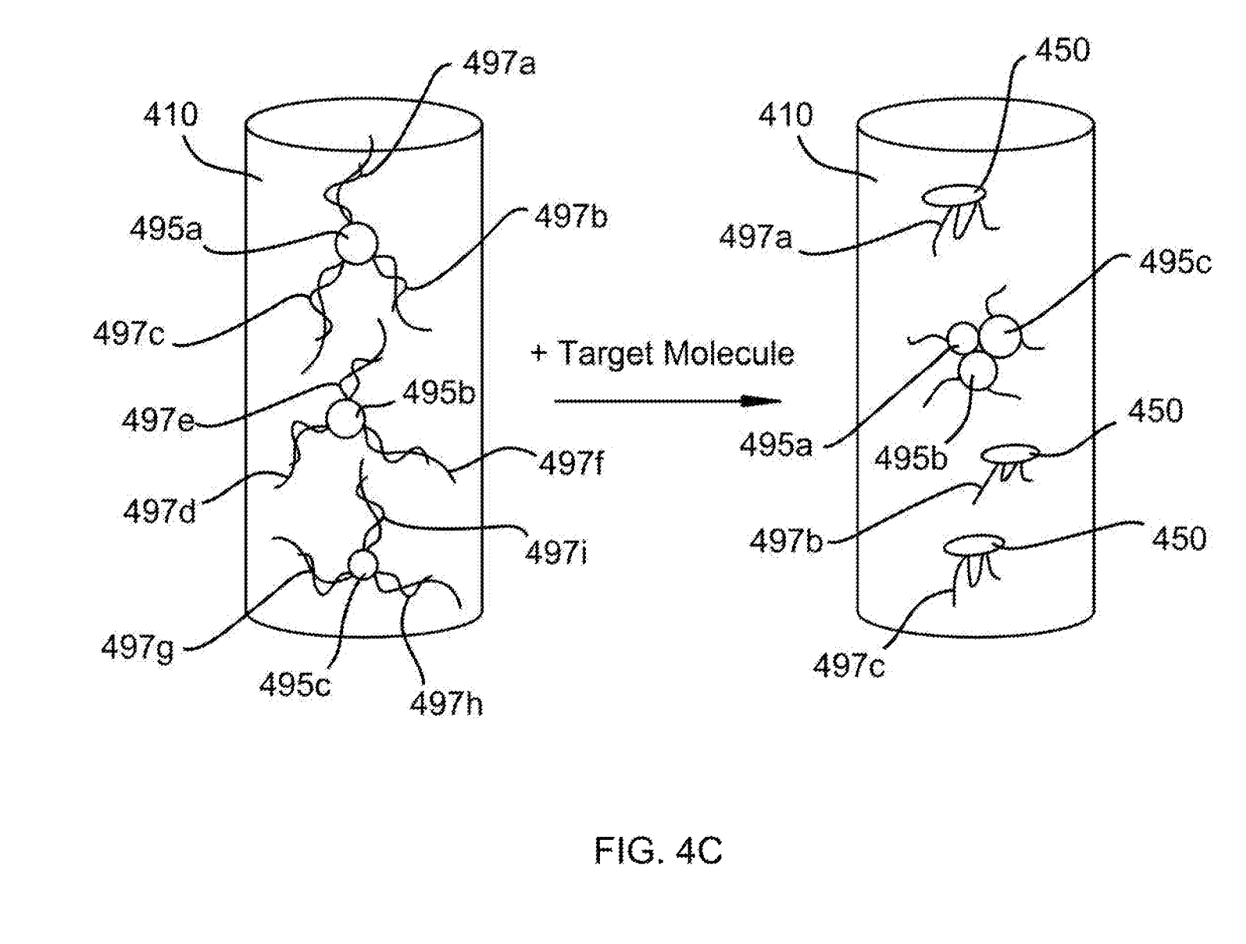
FIG. 4C illustrates an embodiment of and aptamer sensor within a cuvette which produces a colorimetric signal and which may be included in the disclosed in-toilet urinalysis system.

FIG. 4A-C illustrate three types of aptamers which may be included in the disclosed medical toilet. FIG. 4A illustrates an electrochemical aptamer sensor which may be used as a component of the disclosed invention. Cuvette 410 may receive a sample of urine for analysis. Cuvette 410 includes an aptamer that includes electrode 420 which is connected to nucleic acid 430. An electroactive ferrocene label 440 is attached to a terminus of nucleic acid 430. Nucleic acid 430 includes a binding site for a target molecule which may be a component of a user's urine.

As illustrated on the left of FIG. 4A, in the absence of target molecule 450, nucleic acid 430 is relatively flexible and its length positions ferrocene label 440 far enough away from electrode 420 that ferrocene label 440 does not make contact with electrode 420.

As illustrated on the right side of FIG. 4A, nucleic acid 430 folds into a looped configuration when target molecule 450 binds to the binding site on nucleic acid 430. This looped configuration places ferrocene label 440 near electrode 420 thus producing an electrochemical signal.

FIG. 4B illustrates a fluorescent aptamer sensor which may be used as a component of the disclosed invention. The aptamer sensor in cuvette 410 includes single stranded nucleic acid 460 which includes a binding site for target molecule 450 and which is shown in a hairpin configuration. The 5' and 3' termini of single stranded nucleic acid 460 are complementary so that they hybridize to each other creating double stranded section 470. Single stranded hairpin loop 465 is between the complementary 5' and 3' termini. One terminus of single stranded nucleic acid 460 is labeled with fluorophore 480 and the other terminus of single stranded nucleic acid 460 is labeled with quencher 490. The configuration shown on the left side of FIG. 4B occurs in the absence of target molecule 450. In this configuration, quencher 490 is near fluorophore 480 and quenches the fluorescent signal.

As shown in the right side of FIG. 4B, target molecule 450 has bound its binding site within single stranded nucleic acid 460 causing double stranded region 470 to separate. Fluorophore 480 and quencher 490 are consequently separating such that quencher 490 no longer quenches the fluorescent signal of fluorophore 480. A fluorimeter may then read a fluorescent signal emitted by the aptamer.

FIG. 4C illustrates a colorimetric aptamer sensor which may be used as a component of the disclosed invention. The aptamer sensor in cuvette 410 includes aptamers 497a-i which are single stranded nucleic acids and which each include a binding site for target molecule 450. Aptamers 497a-i are hybridized to short, complementary single stranded DNA strands which are bound to nanoparticles 495a, 495b, and 495c. In some embodiments, nanoparticles 495a-c are gold and or other noble metal nanoparticles. As shown in the left side of FIG. 4C, nanoparticles 495a-c are a first color, shown as black.

The right side of FIG. 4C shows the colorimetric aptamer sensor in the presence of target molecule 450. Target molecule 450 has bound its target site within aptamers 497a-i (not all shown for clarity). Upon binding to target molecule 450, aptamers 497a-i change their structure. Nanoparticles 495a-c and their associated short, complementary single stranded DNA strands dissociate from aptamers 497a-i. Nanoparticles 495a-c are unstable in the salt concentration of the urine solution and aggregate. The aggregation causes a color change, shown as white in FIG. 4C. The color change may be detected by an absorption spectrometer within the medical toilet.

Figure 5:
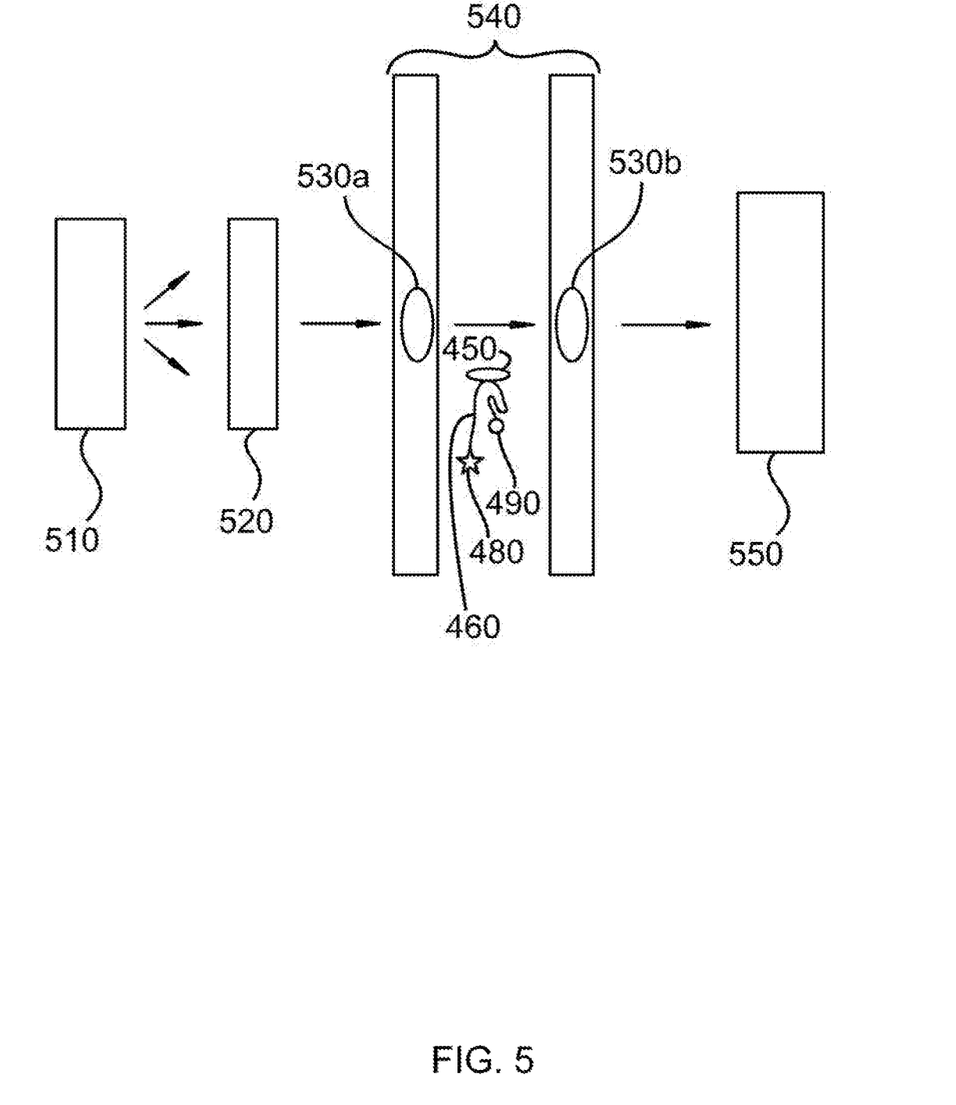
FIG. 5 is a channel within an embodiment of the disclosed in-toilet urinalysis system which includes an optical sensor detecting a fluorescent signal from an aptamer.

FIG. 5 illustrates a fluorescence spectrometer which may be within a medical toilet and which may detect a signal emitted by an aptamer that includes a fluorophore. Channel 540 includes optical windows 530a and 530b and may receive a urine sample. Light source 510 emits light including varied excitation wavelengths as shown by the three arrows pointing in different directions. The light passes through filter 520 which blocks all but one or a range of excitation wavelengths as shown by the single horizontal arrow. The light sequentially passes through optical window 530a, the contents of channel 540, and optical window 530b. Light emitted from optical window 530b is detected fluorimeter 550. Aptamer 460 as presented in the right side of FIG. 4B is shown in channel 450. Aptamer 460 is bound to target molecule 450 and emits a fluorescent signal which may be detected by fluorimeter 550.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

We claim:

1. A medical toilet with an in-toilet urinalysis system, wherein the urinalysis system comprises:
    at least one electrochemical cell, further comprising:
        a counter electrode;
        a functionalized electrode;
        at least one aptamer,
            wherein each of the at least one aptamer is bound to the functionalized electrode, and
            wherein each of the at least one aptamer comprises at least one binding site which binds a component of a user's urine; and
    at least one cuvette for a spectrometric measurement of a signal produced upon binding the component of the user's urine to the at least one aptamer, wherein the cuvette comprises a single opening.

2. The medical toilet of claim 1, further comprising:
    a urine capture reservoir; and
    a channel, wherein the channel fluidly connects the urine capture reservoir to the at least one electrochemical cell.

3. The medical toilet of claim 1, wherein the at least one binding site comprises a plurality of binding sites.

4. The medical toilet of claim 1, comprising a plurality of aptamers, wherein the plurality of aptamers comprises a plurality of unique binding sites, wherein each unique binding site binds a different component of the user's urine.

5. The medical toilet of claim 1, additionally comprising a bias or voltammetry circuit.

6. The medical toilet of claim 5, further comprising a reference electrode, wherein the reference electrode is connected to the bias or voltammetry circuit.

7. The medical toilet of claim 1, further comprising a controller, wherein the controller comprises computer readable medium, and wherein the computer readable medium analyzes signals produced by the at least one aptamer.

8. The medical toilet of claim 1, wherein the functionalized electrode comprises a surface comprising a noble metal selected from the group consisting of ruthenium, rhodium, palladium, silver, osmium, iridium, platinum, and combinations, mixtures, and alloys thereof.

9. The medical toilet of claim 1, wherein the functionalized electrode is located in at least one cuvette.

10. The medical toilet of claim 1, wherein the one or more cuvettes may be moved laterally along a track comprising track rails.

11. The medical toilet of claim 1, wherein the at least one aptamer is functionalized with a ferrocene label.

12. A method to detect a urine analyte in an in-toilet urinalysis system comprising:
    receiving a urine sample from a user in a urine capture reservoir of a toilet;
    directing the urine sample to a functionalized electrode disposed in a cuvette in a spectrometer, the cuvette comprising a single opening;
    binding a urine analyte to a binding site on an aptamer bound to the functionalized electrode; and
    wherein the binding of the urine analyte creates an electrochemical signal that is detected by the spectrometer.

13. The method of claim 12, wherein the urine analyte is a pharmaceutical, protein, drug tag, or a drug marker.

14. The method of claim 12, wherein the functionalized electrode comprises a surface comprising a noble metal selected from the group consisting of ruthenium, rhodium, palladium, silver, osmium, iridium, platinum, and combinations, mixtures, and alloys thereof.

15. The method of claim 12, wherein the cuvette includes a bias or voltammetry circuit.

16. The method of claim 12, further comprising a controller to direct the urine sample to a functionalized electrode and wherein the controller includes computer readable medium which analyzes the electrochemical signal.

17. The method of claim 12, wherein the aptamer is on a protein scaffold.

18. The method of claim 12, further comprising a fluorescent aptamer sensor or a colorimetric aptamer sensor.

19. The method of claim 12, wherein the electrochemical signal is an electric current, voltage shift, or a change in a peak shape of a voltammetry curve.

* * * * *